(12) United States Patent
Gau

(10) Patent No.: US 8,691,065 B2
(45) Date of Patent: Apr. 8, 2014

(54) EFFICIENT INTERFACE BETWEEN ELECTROCHEMICAL SENSOR AND COMPUTER

(75) Inventor: Jen-Jr Gau, Los Angeles, CA (US)

(73) Assignee: GeneFluidics, Inc., Irwindale, CA (US)

( * ) Notice: Subject to any disclaimer, the term of this patent is extended or adjusted under 35 U.S.C. 154(b) by 2069 days.

(21) Appl. No.: 10/954,078

(22) Filed: Sep. 28, 2004

(65) Prior Publication Data

US 2005/0092605 A1   May 5, 2005

Related U.S. Application Data

(60) Provisional application No. 60/517,357, filed on Nov. 4, 2003.

(51) Int. Cl.
*G01N 27/26*   (2006.01)
(52) U.S. Cl.
USPC ..................................... 204/406; 439/620.15
(58) Field of Classification Search
USPC ............................. 204/406; 439/620.15, 913
See application file for complete search history.

(56) References Cited

U.S. PATENT DOCUMENTS

| | | | | |
|---|---|---|---|---|
| 5,120,421 A | * | 6/1992 | Glass et al. | 204/406 |
| 2003/0040881 A1 | * | 2/2003 | Steger et al. | 702/123 |
| 2004/0006265 A1 | * | 1/2004 | Alhussiny | 600/386 |

OTHER PUBLICATIONS

Gau, Jen-Jr. "The enzyme-based electrochemical DNA detector chip using MEMS technology", Dissertation, 2001, University of California, Los Angeles.*
Gau, Jen-Jr, et al. "Enzyme-based electrochemical biosensor with DNA array chip" In Proceedings of the fourth International Symposium on Micro Total Analysis Systems (mTAS), 2000, Enschede, The Netherlands.*
Gau, Jen-Jr, et al. "A MEMS abased amperometric detector for *E. Coli* bacteria using self-assembled monolayers", Biosensors and Bioelectronics, vol. 16, 2001, p. 745-755.*

* cited by examiner

*Primary Examiner* — J. Christopher Ball
(74) *Attorney, Agent, or Firm* — Gavrilovich, Dodd & Lindsey, LLP

(57) ABSTRACT

A system includes one or more electrochemical sensors. Each sensor includes at least two electrodes. The system also includes an interface configured to provide communication between the one or more electrochemical cells and a computer. The interface includes a circuit board with plurality of sensor circuits. Each sensor circuit is configured to operate a different electrochemical sensor and includes a plurality of electrode lines that are each configured to be in communication with a different electrode on an electrochemical sensor.

23 Claims, 7 Drawing Sheets

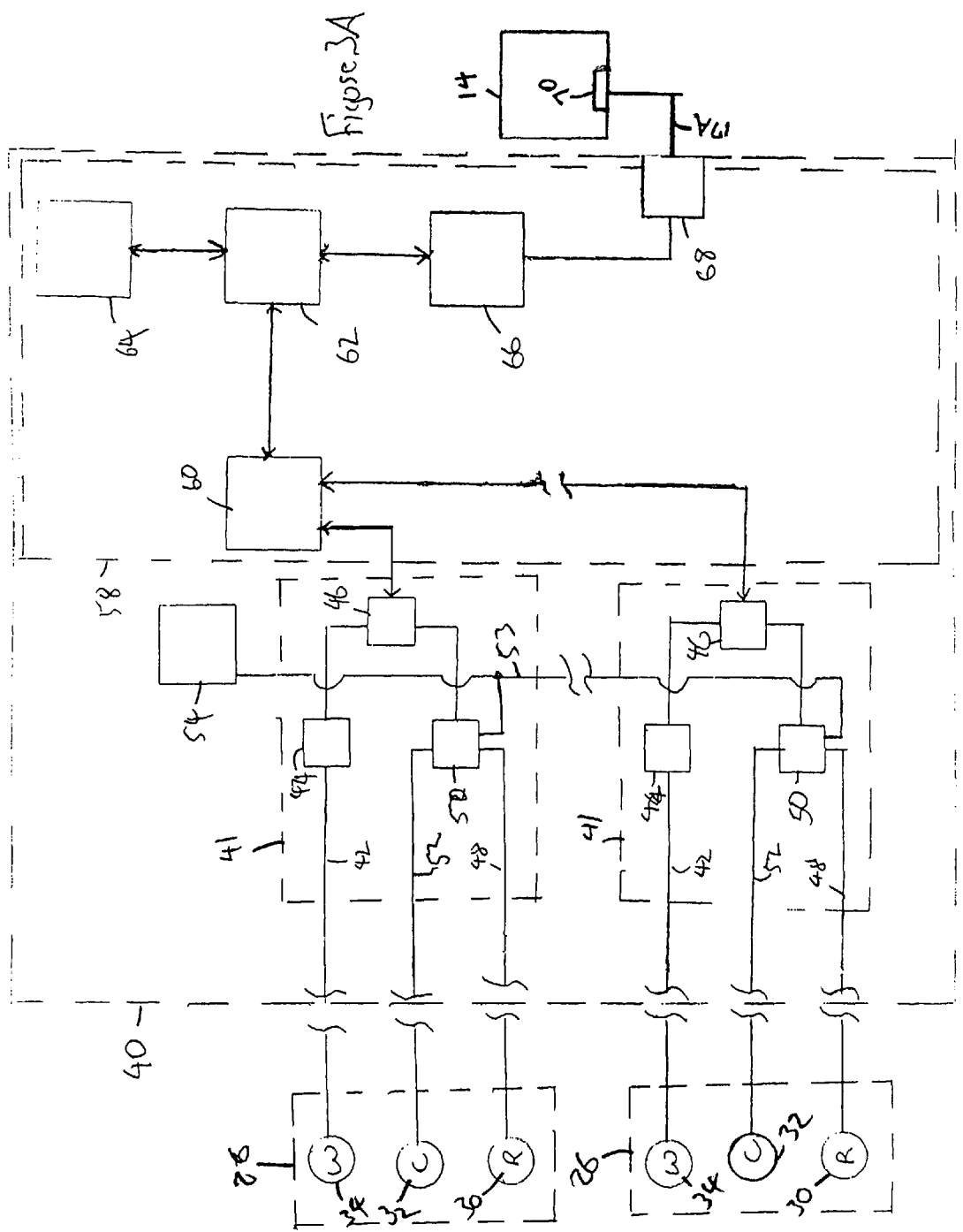

EFFICIENT INTERFACE BETWEEN ELECTROCHEMICAL SENSOR AND COMPUTER

RELATED APPLICATIONS

This application claims priority to U.S. Provisional Patent Application Ser. No. 60/517,357, filed on Nov. 4, 2003, entitled "Efficient Interface Between Electrochemical Sensor and Computer" and incorporated herein in its entirety.

This application is related to U.S. patent application Ser. No. 09/848,727, filed on May 3, 2001, entitled "Biological Identification System With Integrated Sensor Chip" and incorporated herein in its entirety which claims the benefit of U.S. Provisional Application Ser. No. 60/201,603, filed May 3, 2000, entitled "Biological Identification System With Integrated Sensor Chip" and incorporated herein in its entirety.

BACKGROUND

1. Field of the Invention

The invention relates to electrochemical sensors and more particularly to systems for controlling electrochemical sensors.

2. Background of the Invention

Electrochemical sensors can be employed to detect the presence of biological and/or chemical agents in a sample. One version of an electrochemical sensor includes a plurality of electrodes arranged on a substrate. The sample to be tested is positioned on the substrate such that the electrodes are covered by the sample. After the sample is positioned on the sensor, a variety of techniques are available for operating the sensor. In one of these techniques a fixed potential is maintained between two of the electrodes while a current through one of the electrodes is monitored.

A computer can be employed to operate an electrochemical sensor and to store data generated from operation of the sensor. An electronic interface is positioned between the sensors and the computer. The interface allows the computer to communicate with the sensor.

As the performance of these sensors has improved, it has become desirable for a computer to operate a plurality of sensors. Increasing the number of sensors increases the complexity and size of the interface. Further, operating the sensors concurrently increases the amount of data that must be collected by the computer. As a result, there is a need for an efficient and compact interface that allows the computer to operate a plurality of electrochemical sensors.

SUMMARY OF THE INVENTION

An interface between a computer and electrochemical sensors is disclosed. The interface includes a circuit board with one or more sensor circuits. Each sensor circuit is configured to operate a different electrochemical sensor and includes a plurality of electrode lines. Each electrode line is configured to be connected to a different electrode on a single electrochemical sensor. When the board includes a plurality of sensor circuits, the board can also include common electronics that receive and process the signals from a plurality of the sensor circuits.

The interface can be connected to a port on the computer. In some instances, the interface can be connected to an external port on the computer. A suitable external port includes, but is not limited to, a Universal Serial Bus (USB) port. In some instances, the interface can be connected to an internal port on the computer. A suitable internal port includes, but is not limited to, a Peripheral Component Interconnect (PCI) port. In some instances, the interface includes a circuit board that is configured to be inserted into an expansion slot on the computer. A suitable slot includes, but is not limited to, a PCI slot or a USB hub.

A system is also disclosed. The system includes one or more electrochemical sensors that each include at least two electrodes. The system also includes an interface configured to provide communication between the one or more electrochemical cells and a computer. The interface includes a circuit board with a plurality of sensor circuits that are each configured to operate a different electrochemical sensor. Each sensor circuit includes a plurality of electrode lines that are each configured to be in communication with a different electrode on an electrochemical sensor. The system can also include a signal-bearing medium with machine-readable instructions executable by the computer to perform a method of operating the system. In some instances, the method includes collecting data from a plurality of the electrochemical sensors through a single internal port.

In some instances, each sensor circuit is configured to generate a potential difference between at least two electrodes on a sensor. For instance, each sensor circuit can include a working line configured to be in electrical communication with a working electrode on a sensor and a reference line configured to be in electrical communication with a reference electrode on the sensor. The sensor circuit can be further configured to maintain a constant potential differential between the working electrode and the reference electrode. In some instances, each sensor circuit includes a potentiostat. For instance, one or more of the sensor circuits can be configured to a flow a current through an electrode on a sensor so as to maintain a constant potential difference between two other electrodes on the sensor.

BRIEF DESCRIPTION OF THE FIGURES

FIG. 3A is a schematic diagram of electronics that are suitable for use with the interface of FIG. 1A and FIG. 1B.

DETAILED DESCRIPTION OF THE PREFERRED EMBODIMENT

Figure 1A:
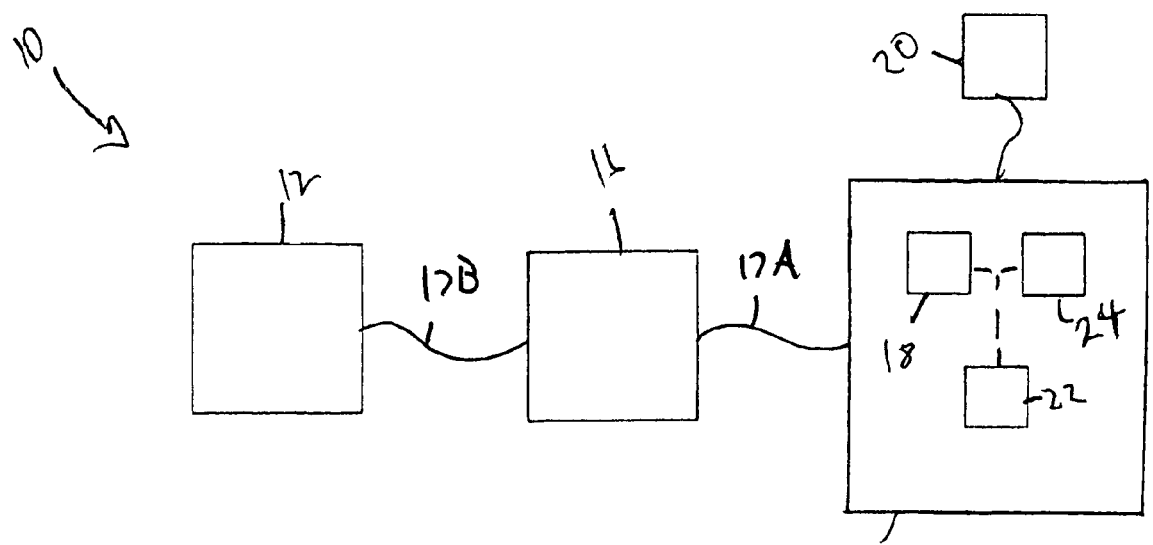
FIG. 1A is a block diagram illustrating a system for operating electrochemical sensors. The system includes a computer and a sensing device. An interface provides communication between the computer and the sensing device.

The invention relates to a system for operating electrochemical sensors. The system can include a sensing device having one or more electrochemical sensors, a computer and software for operating the computer. The system can also include an interface between the computer and sensor. The interface is configured to allow the computer to operate the sensors and to collect data during the operation of the sensors.

The interface can be included a circuit board located in a housing that is positioned external to the computer. In these instances, the interface can include a cable that provides communication between electronics in the interface and an external port on the computer. Alternately, the interface can include a circuit board configured to be inserted into a slot on a computer. For instance, the interface can be an expansion board configured to be inserted into an expansion slot such as a Peripheral Component Interconnect (PCI) slot or a Universal Serial Bus (USB) hub. Accordingly, the sensing device can act as a peripheral device and the interface can act as a controller board for controlling the sensing device.

A suitable sensor for use with the system includes a working electrode, a reference electrode and a counter electrode. The electrodes are positioned on a substrate and are spaced apart from one another. In some instances, a plurality of sensors are included on a single substrate.

The interface can serve as an interface between the computer and a plurality of sensors. In these instances, the board can include a sensor circuit associated with each sensor to be interfaced by the board. Each sensor circuit is configured to generate a potential gradient between electrodes on the associated sensor. For instance, the sensor circuits can each include a potentiostat configured to maintain the potential of a working electrode at a constant level relative to the potential of a reference electrode. Because the board can include a sensor circuit associated with each sensor, the interface can eliminate the need to connect a different interface to the computer for each sensor to be operated by the computer.

During operation of the sensors, the computer collects the data from the sensor circuits. For instance, the computer can collect signals that each represents the current through a working electrode during operation of the sensors. These signals can be collected from the sensor circuit.

When the interface is connected to an internal port and the computer can collect sensor data from the sensor circuits, the data travels only through the internal port but not through an external port such as a serial port, Ethernet port or parallel port. An internal port has a higher speeds and bandwidth than external ports. For instance, a suitable internal port is a Peripheral Component Interconnect (PCI) port or a USB port. A PCI port is connected to a PCI bus. The PCI bus can be implemented as a 64 bit bus or as a 32 bit bus and can run at clock speeds of 33 or 66 MHz. At 32 bits and 33 MHz, it yields a throughput rate of 133 MBps. The enhanced throughput rates associated with these ports allows the interface to provide more efficient data transfer than can be achieved with an external port. Further, the use of an internal port can allow for parallel control and operation of multiple sensors as well as for parallel data transfer.

Additionally, the circuit board can include one or more ports that serve as external ports when the board is inserted into the slot. A plurality of the sensor circuits can be in electrical communication with a single external port. As a result, a single cable can be employed to provide communication between the interface and the sensors. For instance, one or more ribbon cables can be connected to the interface to provide communication between the interface and the sensors. As a result, the interface can reduce the complexity of the system.

As noted above, the interface can be connected to an external port such as a USB port. A USB port allows multiple instrument peripherals to be swapped for one another without turning off the instrument. Additionally, USB ports can send data up to 100 times faster than the 25 pin parallel and DB-9 serial and DB-9 and DB-25 RS-232 serial ports commonly found on computers. These throughput rates allows the interface to provide more efficient data transfer than can be achieved with serial and parallel external ports. Further, the use of a USB port can allow for parallel control and operation of multiple sensors as well as for parallel data transfer.

FIG. 1A is a block diagram illustrating a system 10 for operating electrochemical sensors. The system 10 includes a sensing device 12 that includes one or more electrochemical sensors, a computer 14 and an interface 16. A cable 17A provides electrical communication between the interface and an external port on the computer. The cable 17A can be connected to an external port on the computer such as a USB port. An additional cable 17B provides electrical communication between the interface and the sensing device. The interface provides electrical communication between the computer and the sensing device via the cables 17A and 17B. Although the interface is illustrated as being separate from the sensing device, the interface can be integrated with the sensing device and the cable 17B optionally eliminated.

The computer 14 optionally has access to one or more memories 18 and/or one or more user interfaces 20. The memory 18 can be any memory device or combination of memory devices suitable for read/write operations such as storing images and data developed during execution of code. Suitable user interfaces 20 include, but are not limited to, monitors, printers, mice and keyboards. The one or more memories 18 and/or the user interfaces 20 can be integral with the computer 14 or can peripheral devices.

The computer 14 includes a processor 22 with access to one or more signal bearing media 24 that include machine-readable instructions executable by the processor 22. The processor 22 is preferably a microprocessor. Suitable signal bearing media 24 include, but are not limited to, optical discs such as a compact disk (CD), CD-ROM, CD-R (a recordable CD-ROM that can be read on a CD-ROM drive), CD-RW (multiple-write CD), CD-E (recordable and erasable CD), or DVD (digital video disc). Alternatively, instead of, or in addition to an optical disc, the signal bearing medium 24 may include one or more of the following: a magnetic data storage diskette (floppy disk), a Zip disk, DASD storage (e.g., a conventional "hard drive" or a RAID array), magnetic tape, RAM, electronic read only memory (e.g., ROM, EPROM, or EEPROM), paper punch cards, or transmission media such as digital and/or analog communication links.

In some instances, the signal bearing medium 24 is positioned outside or remote from the computer 14. For instance, the signal bearing medium 24 may be part of, or may be connected to, a server computer that is connected to a computer network. In some instances, the network makes the machine-readable code available to other computers. The network may be a local area network (LAN), a wide area network (WAN), or any other type of network. In some instances, the signal bearing medium 24 may be part of, or may be connected to, a computer that is operating a bulletin board system (BBS), which can be accessed by other computers.

A PC can serve as the computer 14 but would be overqualified in many instances and/or may be undesirably large or bulky. An example of a suitable computer includes a processor speed of 266 MHz or better, a 64 MB or better SDRAM and a 32 MB or better Flash memory.

Figure 1B:
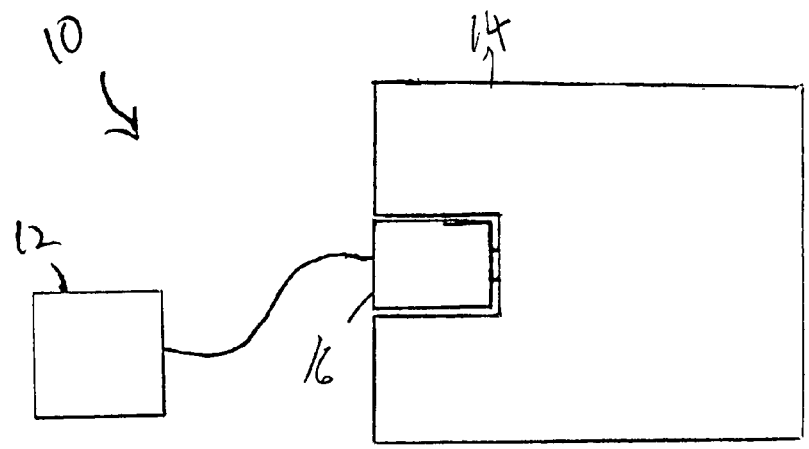
FIG. 1B illustrates the interface of FIG. 1A as a circuit board configured to be inserted into an expansion slot on the computer.

As illustrated in FIG. 1B, the interface 16 can include a circuit board configured to be inserted into a slot on the computer 14. For instance, the interface 16 can be an expansion board configured to be inserted into an expansion slot on the computer 14. The circuit board can be connected to a cable that can be employed to provide electrical communication between the electronics on the circuit board and the sensors on the sensing device 12.

Figure 2A:
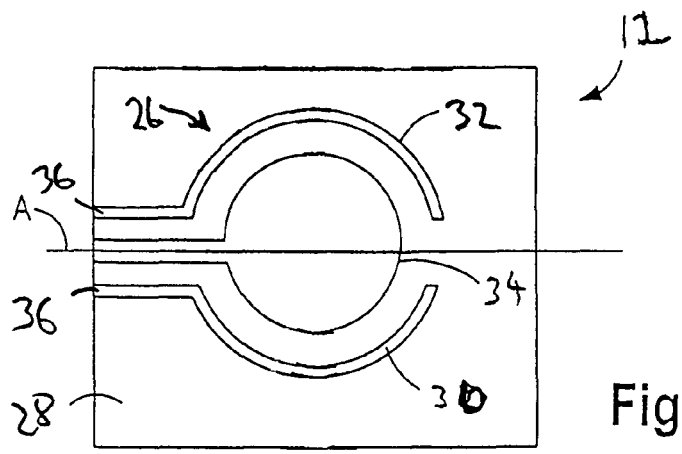
FIG. 2A is a topview of a sensing device having a sensor for detecting the presence of a target agent.
Figures 2B, 2C:
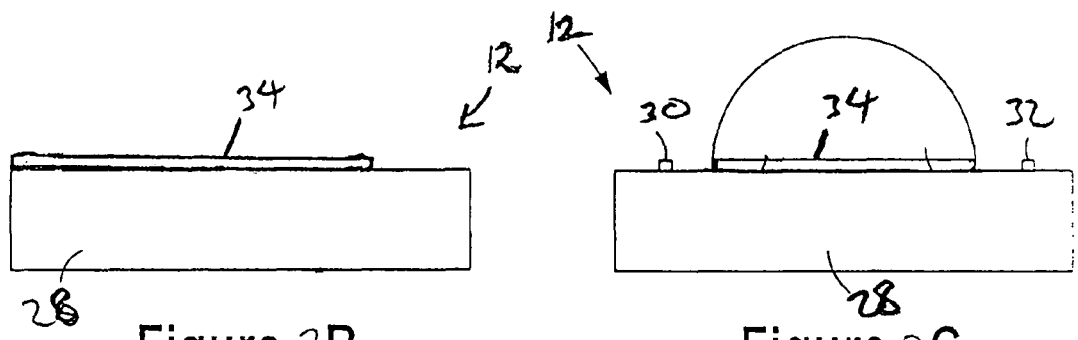
FIG. 2B is a cross section of the sensing device illustrated in FIG. 1A taken along the line labeled A.
FIG. 2C illustrates a sensing device having a sample positioned on a sensor.

FIG. 2A and FIG. 2B illustrates a sensing device 12 that is suitable for use with the system 10 of FIG. 1A and FIG. 1B. FIG. 2A is a topview of the sensing device 12 and FIG. 2B is a cross section of the sensing device 12 shown in FIG. 2A taken at the line labeled A. The sensing device 12 includes a sensor 26 positioned on a substrate 28. A suitable substrate 28 includes, but is not limited to, a silicon substrate. Although the substrate 28 is shown as being constructed from a single material, the substrate 28 can have a composite construction.

The sensor 26 includes a plurality of electrodes that are spaced apart from one another. The electrodes include a reference electrode 30, a counter electrode 32 and a working electrode 34. Each electrode is in electrical communication with a different electrical contact 36. The electrical contacts 36 can be employed to provide electrical communication between the electrodes and the electronics (not shown) in the interface 16. For instance, the electrical contacts 36 can be in electrical communication with the conductors in the cable of FIG. 1B to provide electrical communication between the electronics in the interface 16 and the electrodes on the sensor 26.

The counter electrode 32 and the reference electrodes 30 can have the same shape or can have different shapes. Although the working electrode 34 is shown as having a round shape, the working electrode 34 can have a variety of other shapes including, but not limited to, rectangular shapes. In some instances, each electrode can be constructed from a single layer of material. A suitable material for the electrodes includes gold. Other suitable electrode materials include, but are not limited to, silver, copper, platinum, chromium, aluminum, titanium and nickel.

The working electrode 34 can be constructed such that the largest dimension of the working electrode 34 is less than 4 mm, 1 mm, 100 µm or 50 µm. Suitable widths for the counter electrode 32 and the reference electrode 30 include, but are not limited to, widths less than 20 µm, 100 µm, 0.5 mm or 3 mm. Suitable dimensions for the gap between the working electrode 34 and the reference electrode 30 and/or between the working electrode 34 and the counter electrode 32 include, but are not limited to, gaps less than 1 µm, 100 µm, 0.5 mm or 2 mm. These dimensions can provide for a sensor 26 having a compact size.

During operation of the sensors 26, a sample is positioned on the sensor 26 as illustrated in FIG. 2C. The sample concurrently contacts the working electrode 34, the reference electrode 30 and the counter electrode 32. Surface tension serves to preserve the shape of the test volume as well as to keep the test volume positioned over the electrodes.

The above sensing device 12 can be included in a cartridge (not shown). In some instances, the cartridge can be employed to deliver liquids onto the sensors and/or to form the sample on the sensors. Examples of sensor and cartridge constructions are provided in U.S. patent application Ser. No. 10/288,320, entitled "System For Detection of a Component in a Liquid," filed on Nov. 4, 2002 and incorporated herein in its entirety.

A variety of techniques can be employed to operate a sensor 26 constructed according to FIG. 2A through FIG. 2C. In one technique known as Potentiostatic Coulometry, the working electrode 34 is held at a constant potential relative to the reference electrode 30. The potential gradient in the sample is held at a level sufficient to cause electron transfer between the working electrode 34 and at least one component in the sample. The electron transfer allows current to flow through the working electrode 34. Because the amount of the component in the sample changes over time, the current level through the working electrode 34 also changes with time. During operation of the sensor 26, the potential difference between the working electrode 34 and the reference electrode 30 is maintained at a constant level while the current through the working electrode 34 is measured.

Figure 2D:
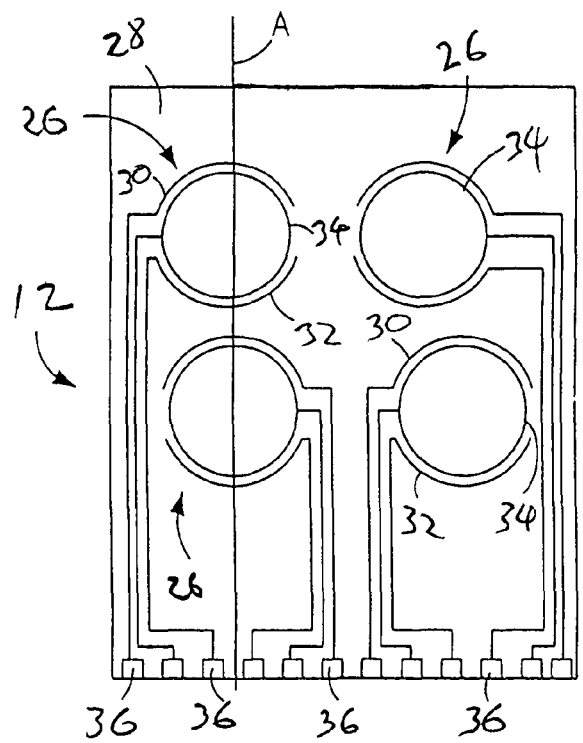
FIG. 2D illustrates a sensing device having a plurality of sensors.

Although FIG. 2A through FIG. 2C illustrate the sensing device 12 as having a single sensor 26, a sensing device 12 can include a plurality of sensors 26 as illustrated in FIG. 2D. The sensors 26 can be arranged in an array on the sensing device 12. Each of the sensors 26 includes a working electrode 34, a reference electrode 30 and a counter electrode 32. Different sensors 26 on the sensing device 12 can be operated concurrently or serially. Each sensor 26 can be employed to test for the presence of a different target agent. As a result, the sensing device 12 can provide highly efficient testing for a plurality of different target agents. Alternatively, multiple sensors 26 can be employed to test for the presence of the same target agent. The multiple tests can serve as a redundancy check or the tests performed on each sensor 26 can be for target agents in different samples.

FIG. 3A is a schematic diagram of electronics 40 that are suitable for use with the interface 16 of FIG. 1A and FIG. 1B. The interface electronics 40 include a plurality of sensor circuits 41 that are each associated with a sensor 26 to be operated via the interface. Accordingly, each sensor circuit 41 can be in electrical communication with a different sensor 26 on a sensing device 12. The number of sensor circuits 41 can be from 1 to n depending on the number of sensors 26 to be operated by the interface.

Each sensor circuit 41 includes electronics configured to generate a potential between electrodes on the associated sensor 26. For instance, the sensor circuit 41 can include a potentiostat configured to maintain a constant potential difference between the working electrode 34 and the reference electrode 30 of a sensor 26 constructed according to FIG. 2A.

The sensor circuits 41 include a working line 42 configured to be in electrical communication with a working electrode 34. The working line 42 is also in electrical communication with amplification electronics 44. The amplification electronics 44 are configured to amplify the voltage of the signal on the working line 42. Accordingly, the amplification electronics 44 amplify the voltage of the signal from the working electrode 34. In some instances, the amplification electronics 44 are also configured to apply a resistance to the amplified signal. Further, the amplification electronics 44 can be configured such that the computer can control the level of resistance applied to the amplified signal in response to the signal strength.

The amplified signal from the amplification electronics 44 is output to an analog to digital converter (ADC) 46 where the analog signal from the amplification electronics 44 is converted to a digital signal. The computer receives the digital amplified signal after some additional processing and can use the signal to determine the level of current flow through the working electrode 34.

Each sensor circuit 41 also includes a reference line 48 configured to be in electrical communication with the reference electrode 30. The reference line 48 is also in electrical communication with potential control electronics 50. Additionally, each sensor circuit 41 includes a counter line 52 configured to be in electrical communication with the counter electrode 32. The counter line 52 is also in electrical communication with the potential control electronics 50.

The potential control electronics 50 are in electrical communication with the ADC 46.

The potential control electronics 50 in each sensor 26 are also in electrical communication with a signal line 53. The signal line 53 is in electrical communication with a signal source 54 that is configured to be controlled by the computer. The signal source 54 generates a source signal that is received by the potential control electronics 50 and serves as the source of the signal applied to the counter electrode 32 and the reference electrode 30. A suitable signal source 54 includes, but is not limited to, a 16 bit digital-to-analog converter (DAC) such as a 16 bit DAC.

During operation of the sensors 26, the potential control electronics 50 receive the source signal from the signal source 54. The potential control electronics 50 employ this signal to generate a signal that is applied to the reference electrode 30 so as to generate a potential at the reference electrode 30. At the same time, a potential is not applied to the working electrode 34. The potential gradient formed between the working electrode 34 and the reference electrode 30 is held at a level sufficient to cause electron transfer between the working electrode 34 and at least one component in a sample positioned on the sensor 26. The electron transfer allows current to flow through the working electrode 34. In response to changes in the potential difference between the reference electrode 30 and the working electrode 34, the potential control electronics 50 flow a current through the counter electrode 32 such that the potential differential is returned to the initial level. As a result, the amplification electronics 44 and the potential control electronics 50 together to serve as a potentiostat.

Each sensor circuit 41 is in electronic communication with common electronics 58. The ADC 46 from each sensor circuit 41 is in electrical communication with a board memory 60. A suitable board memory 60 includes, but is not limited to, RAM. In some instances, the board memory 60 is a FIFO memory such as an 8192X16 FIFO.

The board memory 60 is in electrical communication with a digital signal processor (DSP) 62. The DSP 62 can allow for any additional signal processing that is desired before the signals from the sensor circuits 41 are provided to the computer. For instances, the DSP 62 can be employed for process the data, performing calculations on the data and data modulation. A suitable DSP 62 can handle the parallel processing of data from multiple sensors 26 or multiple channels. An example of a suitable DSP 62 includes, but is not limited to, a TMS320C6721 sold by Texas Instrument located in Dallas, Tex. In some instances, the DSP 62 has access to a DSP memory 64. The memory can be used to store a program and/or data for use by the DSP 62. A suitable DSP memory 64 includes, but is not limited to, a random access memory (RAM), FIFO memory, FPGA module or shift register. In some instances, the DSP memory 64 is a static random access memory (SRAM) such as 512 Kbyte SRAM 4 bit Flash.

The DSP 62 is in electrical communication with control logic 66. The control logic 66 can provide data management and allows the computer to control various components of the interface. Additionally, the control logic 66 can include a buffer for managing the transfer of data to the computer. The control logic 66 that is suitable for use in the interface can be a function of the technology employed to connect the interface to the computer. For instance, if the interface is to be connected with a PCI interface, suitable control logic 66 includes the electronics that are typically employed in conjunction with a PCI interface. An example of control logic 66 suitable for use with a PCI interface includes a PCI 9030 sold by Plxtech located in Sunnyvale, Calif.; an LogiCORE PCI 64 sold by Xilinx located in San Jose, Calif. and an Spartan-3 FPGA with PCI module sold by Xilinx located in San Jose, Calif. If the interface is to be connected with a USB interface, suitable control logic 66 includes the electronics that are typically employed in conjunction with a USB interface. An example of control logic 66 suitable for use with a USB interface includes a C8051F320 sold by Silicon Laboratories located in Austin, Tex.; a PDIUSBD11 sold by Phillips located in Eindhoven, the Netherlands and an AT43USB325 sold by ATMEL located in San Jose, Calif.

The control logic 66 is connected to computer interface electronics 68 that serve to connect the interface with the computer. The computer interface electronics 68 can include a connector that connects the interface to a port 70 in the computer or to a cable that provides electrical communication between the computer interface electronics 68 and the port 70 on the computer. For instance, the one or more connectors can be a USB connector and/or configured to be coupled with a cable having a USB connector. The port 70 can be an external port such as a USB port or an internal port such as a PCI port.

Internal ports are ports that are typically included on a motherboard and/or are connected to a local bus. For instance, suitable internal ports 70 are Peripheral Component Interconnect (PCI) ports, a compact Peripheral Component Interconnect (cPCI) ports, an Industry Standard Architecture (ISA) ports, PCMCIA ports and Universal Serial Bus (USB) hubs. The use of the term "internal" in "internal port" does not necessarily refer to the location of the port. For instance, PCI-to-PCI expansion technology is available which makes a PCI port externally accessible. An example of this technology is sold by Magma, Inc. located in San Diego, Calif. The computer interface can be employed in conjunction with internal ports that are externally accessible. Additionally, USB ports are generally external ports but can be internal ports as a USB hub. An example of this technology is sold by Starmount Limited located in Lancs, UK.

The interface electronics 40 illustrated in FIG. 3A can be included in a housing that is positioned external to the computer. In these instances, a cable can connect the computer interface electronics 68 to the port 70. All or a portion of the interface electronics 40 can be positioned on a circuit board in the housing.

Figure 3B:
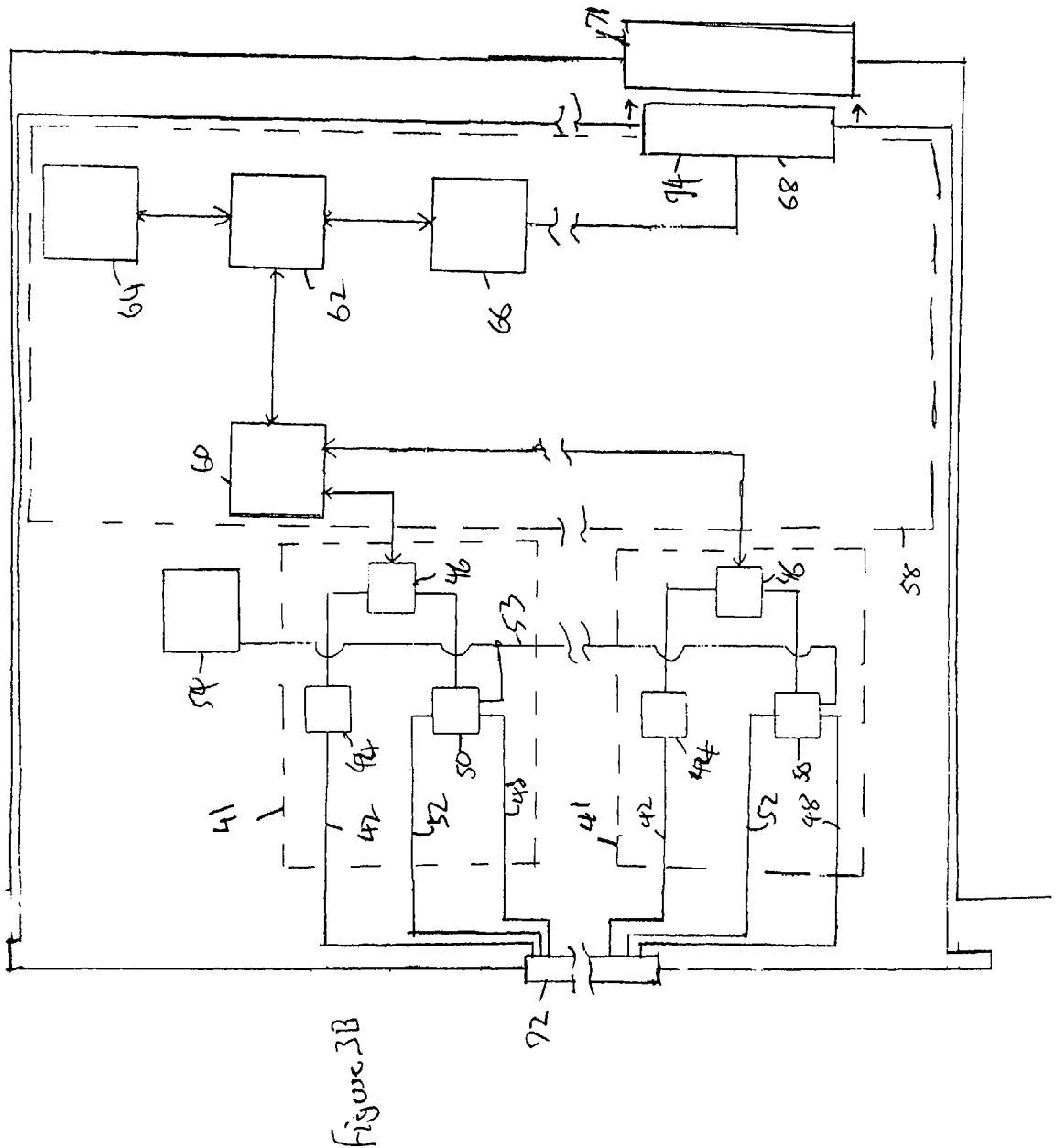
FIG. 3B illustrates the electronics of FIG. 3A included on a circuit board that is configured to be inserted into an expansion slot on a computer.

The interface electronics 40 of FIG. 3A can be included on a circuit board that is configured to be inserted into a slot on a computer as illustrated in FIG. 3B. A suitable slot includes but is not limited to, a Peripheral Component Interconnect (PCI) slot, a compact Peripheral Component Interconnect (cPCI) slot, an Industry Standard Architecture (ISA) slot, a PCMCIA slot, or a USB hub. Although all of the interface electronics are shown positioned on the circuit board, the interface electronics need not all be positioned on the circuit board.

The working lines 42, the counter lines 52 and the reference lines 48 are each in electrical communication with a pin in one or more external ports 72. The one or more external ports 72 are configured to be connected to a cable such as a ribbon cable. The cable can be employed to provide electrical communication between each of the lines and the electrodes on the associated sensor. For instance, the cable can be employed to connect the working line 42, the reference line 48 and the counter line 52 of a single sensor circuit 41 with the working electrode 34, the reference electrode 30 and the counter electrode 32 of a single sensor. The connection can be direct, indirect and/or temporary. For instance, the conductors in the ribbon cable can be soldered to electrical contacts on the sensing device. Alternately, the ribbon cable can be connected to a device having pogo pins that can be temporarily contacted with electrical contacts on the sensing device. Suitable external ports 72 include, but are not limited to, serial ports, parallel ports and USB ports, ISA and PCI.

The control logic 66 is in electrical communication with the one or more connectors 74. The one or more connectors 74 are configured to be coupled with an internal port 71 located within the slot. For instance, the one or more connectors 74 can be configured to be coupled with a, a PCI port or an ISA port or a USB hub.

The electronics 40, the one or more external ports 72 and the one or more connectors 74 can be formed on the board employing traditional integrated circuit manufacturing techniques.

Figure 4A:
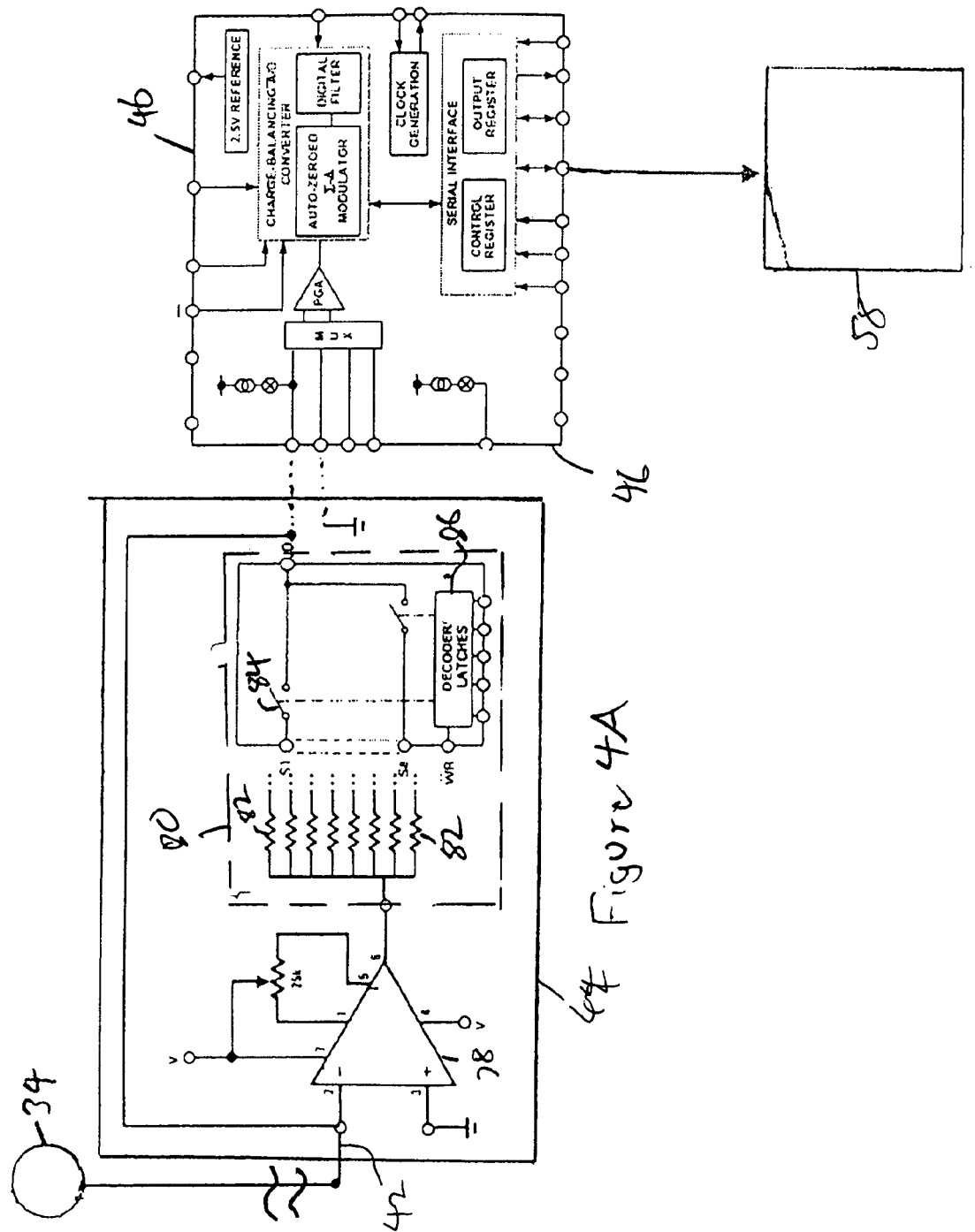
FIG. 4A is a schematic diagram of a circuit that is suitable for use as amplification electronics in the electronics of FIG. 3A and FIG. 3B.

FIG. 4A is a schematic diagram of a circuit suitable for use as the amplification electronics 44 of FIG. 3A and/or FIG. 3B. The working line 42 is connected to the inverting input of an operational amplifier 78 with variable gain. The non-inverting input is grounded. The output of the amplifier 78 is connected to a resistance selector 80 for providing a variable resistance level that can be controlled by the computer. The output of the resistance selector 80 is carried on an output line connected to the ADC 46. A feedback line extends between the output line and the working line 42.

The resistance selector 80 includes a plurality of resistors 82 connected in parallel. All or a portion of the resistors 82 can be different from one another. A switch 84 is connected in series with each resistor 82. One or more of the switches 84 can be closed so as to control the level of resistance provided by the resistance selector 80. The switches 84 are controlled by decoder latches 86 which are configured to receive a digital signal from the computer indicating which of the switches are to be opened and closed. Accordingly, the computer can select the level of resistance provided by the resistance selector 80.

During operation of the circuit illustrated in FIG. 4A, the working line 42 carries the signal from the working electrode 34. The amplifier 78 amplifies the signal before it is passed to the resistance selector 80. The computer sends a digital signal to the decoder latches 86 to select a particular resistance level and then samples the amplified signal. If the signal is too weak or strong, the computer sends another digital signal to the decoder latches 86 to select a different resistance level. These steps are repeated until the desired signal strength is achieved.

Figure 4B:
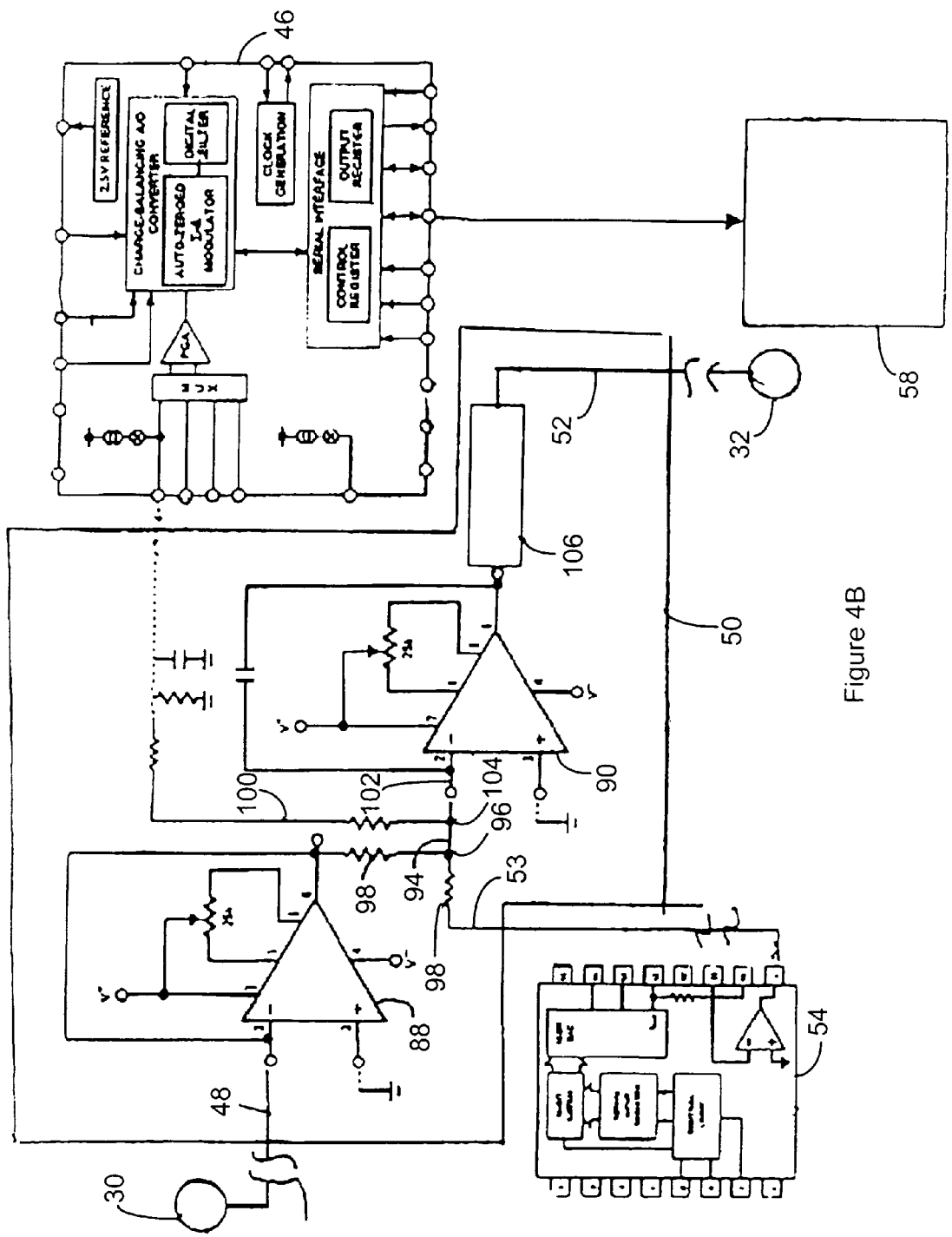
FIG. 4B is a schematic diagram of a circuit that is suitable for use as potential control electronics in the electronics of FIG. 3A and FIG. 3B.

FIG. 4B is a schematic diagram of a circuit suitable for use as the potential control electronics 50 of FIG. 3A and FIG. 3B. The circuit includes a first amplifier 88 connected in series with a second amplifier 90. The first amplifier 88 is configured to serve as voltage follower. The second amplifier 90 is an inverting integrating operational amplifier with adjustable gain. The working line 42 is connected to the inverting input of first amplifier 88 and the non-inverting input is grounded. The output of the first amplifier 88 is carried on a first output line.

A signal line 53 is in electrical communication with a signal source 54. The signal line 53, the first output line and a transition line 94 are connected at a first node 96. The first output line and the signal line 53 each include a resistor 98. The resistance provided by the resistors 98 can be the same or different. In one example, the resistors 98 are each 10 kΩ resistors.

The transition line 94, a converter line 100 and a second input line 102 are connected at a second node 104. The converter line 100 is in communication with the ADC 46.

The second input line 102 is connected to the inverting input of the second amplifier 90 and the non-inverting input is grounded. The output from the second amplifier 90 is carried on a counter line 52 and serves as the counter signal that is applied to the counter electrode 32. A relay 106 is positioned along the counter line 52 and acts as a switch that permits the computer to switch the counter signal on and off.

The electronics associated with the first amplifier 88 act as a voltage follower and the electronics associated with the second amplifier 90 serve as a feedback loop. During operation of the potential control electronics 50 illustrated in FIG. 3B, the potential control electronics 50 receive a source signal on the source line. When the resistors 98 provide the same level of resistance, the first amplifier 88 adjusts the output current such that the potential of the reference electrode 30 is maintained at the potential of the source signal. Accordingly, the current through the counter electrode 32 is adjusted so as to maintain the reference electrode 30 and the source signal at about the same potential. For instance, when the potential at the reference electrode 30 and the source signal have the same potential, the potential at the first node 96 is non-zero there is no current through the counter electrode 32. When the potential at the reference electrode 30 changes relative to the potential of the source signal, the output current of the first amplifier 88 is changed such that the potential at the first node 96 is non-zero. As a result, a potential is applied to the input of the second amplifier 90 and a current flows through the counter electrode 32.

Because the electronics maintain the potential of the reference electrode 30 at the potential of the source signal, the potential of the reference electrode 30 can be maintained at a constant potential by generating a source signal with a constant potential. Further, a potential is not applied to the working electrode 34 during the operation of a sensor. As a result, the circuits illustrated in FIG. 4A and FIG. 4B maintain a substantially constant potential difference between the reference electrode 30 and the working electrode 34 during operation of the sensor.

Figure 5:
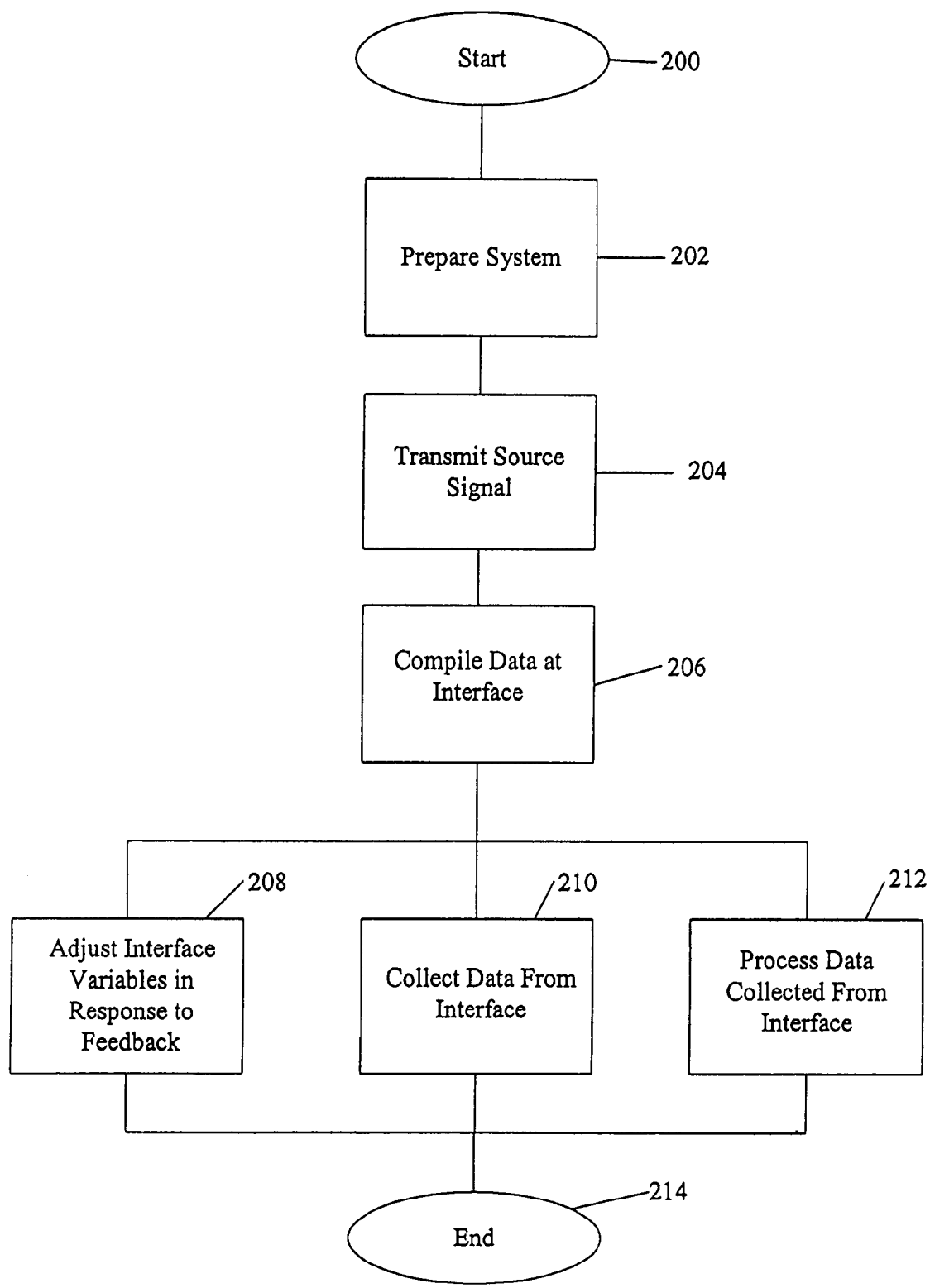
FIG. 5 illustrates a method for operating the system of FIG. 1A and FIG. 1B.

FIG. 5 illustrate a method for operating one or more sensors 26 constructed according to FIG. 2A through FIG. 2D. The method is started at block 200. The method can be started by a user initiated command at a user interface 20 on the computer 14 of FIG. 1A or FIG. 1B.

At block 202, the interface is prepared for operation. For instance, the computer transmits a signal to the signal source 54 illustrated in FIG. 3A. The signal indicates the characteristics of the source signal to be produced during operation of the sensors. Suitable source signals include, but are not limited to, a source signal with a constant potential or a signal with a ramping potential.

At block 204, the source signal is transmitted from the signal source 54. For instance, the computer can transmit a signal to the signal source 54 to begin transmission of the source signal. Additionally, the computer can transmit a signal to the relay 106 of FIG. 4B to allow current to flow through the counter electrode 32.

At block 206, the interface begins compiling data. For instance, the computer can transmit a trigger signal to the board memory 60 of FIG. 3A to trigger collection of data from the ADCs 46. The trigger signal can be transmitted to the board memory 60 before or after the transmission of the source signal at block 204.

At block 208, adjustments are made to the variables on the interface in response to data collected from the interface. For instance, the computer can sample the strength of the signal received from the amplification electronics 44 shown in FIG. 3A. If the signal strength is not appropriate, the computer can change the level of resistance applied to that signal. When the interface includes amplification electronics 44 according to FIG. 4A, the computer can change the resistance by sending a signal to the decoder latches 86 of FIG. 4A to change the selection of switches that are closed. The operations at block 208 can be repeated throughout operation of the sensors. As a result, the variables can be adjusted throughout the operation of the sensors.

At block 210, the computer collects data from the electronic interface. For instance, the computer can send a signal to the control logic 66 of FIG. 3A to initiate transfer of data from the board memory 60 into the computer. Because the interface includes a plurality of sensor circuits 41, the computer can concurrently collect the data for a plurality of the sensors through a single internal port.

At block 212, the computer can process the data received from the interface. For instance, the computer can act as an integrator that employs the signal data from the each working electrode 34 to determine the current through that working electrode 34. The computer can additionally coulometric techniques to determine the presence and/or concentration of one or more agents in the sample positioned on each sensor. The computer can use one or more of the user interfaces to display the results to the user.

The method ends at block 214. The method can end in response to a user input at a user interface. Alternately, the method can end as a result of one or more conditions being satisfied. For instance, the method can end in response to a time limit expiring or in response to the signal strength from each of the working electrodes 34 falling below some limit.

Although block 206 through block 212 are shown occurring concurrently, one or more of these operations can be performed serially. For instance, the computer may process the data after all the data is collected. Further, the operations at block 210 are optional. For instance, the computer can store the collected data in a memory and process the collected date at a later time.

As noted above, the computer has access to one or more signal bearing media that include machine-readable instructions executable by a processor. The above method can be encoded into these instructions.

Although FIG. 3A and FIG. 3B illustrate a plurality of sensor circuit 41 receiving a source signal from a single signal source 54, the interface can be configured such that different sensor circuits 41 receive a different source signal. For instance, each of the sensor circuits 41 can include a different signal source 54. As a result, the source signal employed by different sensor circuits 41 can be different. The use of different source signals allows a different type of experiment to be performed at different sensors.

Although the systems are shown above as including a single sensing device, the system can include a plurality of sensing devices connected to a single interface. Each of the sensing devices can include one or more sensors.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. An interface between a computer and electrochemical sensors, comprising:

a circuit board including
  a plurality of sensor circuits that are each configured to operate a different electrochemical sensor where each of the sensors includes a different reference electrode and the reference electrode included in each sensor is one of multiple electrodes included in the sensor,
  each sensor circuit including a plurality of electrode lines that are each configured to be in communication with the electrodes included in each of the electrochemical sensors; and
  common electronics that receive and process signals from a plurality of the sensor circuits.

2. The interface of claim 1, wherein each sensor circuit is configured to generate a potential difference between at least two of the electrodes on a sensor.

3. The interface of claim 1, wherein each sensor circuit includes a potentiostat.

4. The interface of claim 1, wherein the electrodes included in each sensor include a working electrode and each sensor circuit includes a working line configured to be in electrical communication with the working electrode included in the sensor and a reference line configured to be in electrical communication with the reference electrode included in the sensor, the sensor circuit being further configured to maintain a constant potential differential between the working electrode and the reference electrode included in each of the sensors.

5. The interface of claim 1, wherein one or more of the sensor circuits is configured to a flow a current through an electrode on a sensor so as to maintain a constant potential difference between two other electrodes on the sensor.

6. The interface of claim 1, wherein one or more of the sensor circuits is configured to apply a potential to one electrode of a sensor without applying a potential to another electrode of the sensor.

7. The interface of claim 1, wherein one or more of the sensor circuits includes a first amplifier connected in series with a second amplifier.

8. The interface of claim 1, wherein the board is configured to be connected to an internal port in a computer.

9. The interface of claim 8, wherein the internal port is a Peripheral Component Interconnect (PCI) port.

10. The interface of claim 8, wherein the internal port is a Universal Serial Bus (USB) hub.

11. The interface of claim 1, wherein the circuit board is configured to be inserted into a slot on a computer.

12. The interface of claim 11, wherein the slot is an expansion slot.

13. The interface of claim 12, wherein the expansion slot is a Peripheral Component Interconnect (PCI) slot.

14. The interface of claim 12, wherein the expansion slot is a Universal Serial Bus (USB) hub.

15. The interface of claim 11, wherein each sensor circuit is configured to generate a potential difference between at least two of the electrodes on a sensor.

16. The interface of claim 11, wherein each sensor circuit includes a potentiostat.

17. The interface of claim 11, wherein the electrodes included in each sensor include a working electrode and each sensor circuit includes a working line configured to be in electrical communication with the working electrode included in the a sensor and a reference line configured to be in electrical communication with the reference electrode included in the sensor, the sensor circuit being further configured to maintain a constant potential differential between the working electrode and the reference electrode included in each of the sensors.

18. The interface of claim 11, wherein one or more of the sensor circuits is configured to a flow a current through an electrode on a sensor so as to maintain a constant potential difference between two other electrodes on the sensor.

19. The interface of claim 11, wherein one or more of the sensor circuits is configured to apply a potential to one electrode of a sensor without applying a potential to another electrode of the sensor.

20. The interface of claim 11, wherein one or more of the sensor circuits includes a first amplifier connected in series with a second amplifier.

21. The system of claim 1, wherein the circuit board is configured to operate the electrochemical sensors concurrently.

22. The system of claim 1, wherein the reference electrode included in each one of the sensors is not shared with any of the other sensors.

23. The system of claim 1, wherein the sensors are included on a sensing device that is separate from the circuit board and the sensing device does not include electrical connections between any of the reference electrodes included in the sensors.

* * * * *